United States Patent [19]

Lee

[11] 4,208,340

[45] Jun. 17, 1980

[54] SUBSTITUTED ORTHO-QUINONES AND DERIVATIVES

[75] Inventor: Richard J. Lee, Downers Grove, Ill.

[73] Assignee: Standard Oil Company (Indiana), Chicago, Ill.

[21] Appl. No.: 955,930

[22] Filed: Oct. 30, 1978

[51] Int. Cl.$^2$ .................. C07C 49/62; C07C 49/73; C07C 49/735

[52] U.S. Cl. .............................. 260/396 R; 544/399

[58] Field of Search .................... 544/399; 260/396 R

[56] References Cited

U.S. PATENT DOCUMENTS

T917,001  12/1973  Anderson et al. ............... 260/396 R

*Primary Examiner*—Jose Tovar
*Attorney, Agent, or Firm*—William H. Magidson; William T. McClain

[57] ABSTRACT

Ortho-quinones with alkyl, olefin polymer, or halogen substituents and a process for the preparation of these compounds comprising a base catalyzed halogen oxidation of alkylated phenol.

5 Claims, No Drawings

SUBSTITUTED ORTHO-QUINONES AND DERIVATIVES

This invention relates to substituted ortho-quinone compounds. More particularly this invention relates to ortho-quinones with alkyl, olefin polymer, or halogen substituents, and to a process for the preparation of these compounds wherein alkylated phenol is oxidized by a halogen compound in the presence of a base catalyst.

Ortho-quinones are useful as intermediates in the production of several types of compounds such as anti-oxidants, rust inhibitors, insecticides, fungicides, and ultraviolet absorbers. Substituted ortho-quinones traditionally have been generated by the introduction of oxygen into a suitably substituted phenol or by the oxidation of catechol derivatives. For example, the oxidation of chlorinated catechols to prepare mono- and dichlorinated ortho-quinones is disclosed by Willstatter, *Chem. Ber.*, 44, 2182, 1911. Several different substituted phenols have been oxidized to ortho-quinones by the alkali salts of nitrosodisulphonate. Teuber and Staiger, *Chem. Ber.*, 88, 802, 1955. An extensive review of the synthesis and thermal reactions of ortho-quinones covering the years 1947-1967 has been made by W. M. Horspool. *Quarterly Reviews*, No. 2, Vol. 23, p. 204, 1969. Both the introduction of oxygen into phenols and the oxidation of catechol derivatives are throughly discussed and referenced. Gess and Dence in Tappi, 54(7), 1114-21, 1971 discuss the preparation of chloromethylortho-quinones from creosol through chlorination with subsequent cleaving of the ether linkage of the methoxy substituent. The preparation of completely dehydrogenated quinones is disclosed in U.S. Pat. No. 3,479,374. The class of alkylated ortho-quinones of the present invention however has not been disclosed because the traditional oxidation methods are not desirable for generating these novel compounds. Previously known oxidation methods, especially those involving acid catalysis, tend to cause dealkylation of aliphatic substituents of about twelve or more carbon atoms during the oxidation process. A need exists for ortho-quinone compounds with substituents of the size and for a process for their preparation because of the large number of useful derivatives that can be generated from them.

The object of this invention is to provide a new class of ortho-quinone compounds. A further object is to provide a halogen oxidation process for the preparation of these quinone compounds. Another object is to provide useful quinone intermediates for the generation of several types of derivative compounds. Other objects appear hereinafter.

We have found that it is possible to produce a new class of substituted ortho-quinone compounds comprising alkylated ortho-quinones and alkylated halogenated ortho-quinones by a base catalyzed halogen oxidation of an alkylated phenol. As indicated above, these ortho-quinone compounds are useful intermediates in the production of anti-oxidants, rust inhibitors, insecticides, fungicides, and ultraviolet absorbers.

The compounds of the present invention are substituted ortho-quinones having the structure:

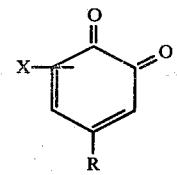

wherein R is an aliphatic chain, preferably a hydrocarbyl chain of at least 12 carbon atoms, such as a $C_{12}$ or higher branched or straight chained alkyl or a $C_3$ or higher olefin polymer with $\overline{M}_n$ of about 170 to about 2100; and X is hydrogen or halogen such as, chlorine, bromine, or iodine. Preferably when R is a polymer substituent it comprises a tetramer or higher homolog of polypropylene or polybutene. The halogen group, when present, renders the ortho-quinone more reactive since the compound is then capable of facile substitutions by virtue of the labile halide function. The halogenated ortho-quinones are therefore especially useful in generating derivatives containing the corresponding alkyl or polymer substituent.

The alkylated ortho-quinone compounds can be produced by the oxidation of a monoalkylated meta or paraphenol by a halogen compound in the presence of a base catalyst. This method of oxidation is also a means of halogenation to obtain the halogenated alkylated ortho-quinone compounds. The reaction is believed to be an ionic one via a phenate ion mechanism rather than a free radical reaction because the aliphatic substituent on the phenol reactant remains intact on the ortho-quinone generated. This permits selectivity in the generation of a quinone intermediate for a specific derivative application.

Alkylated phenols suitable as reactants include meta or paraphenols wherein the substituent comprises an aliphatic chain, preferably a hydrocarbyl chain of at least 12 carbon atoms, such as a $C_{12}$ or higher straight chained or branched alkyl group like dodecyl, tridecyl, tetradecyl, pentadecyl, octadecyl and similar groups, or a $C_3$ or higher olefin polymer of $\overline{M}_n$ from about 170 to about 2100 such as a tetramer or higher homolog of polypropylene or polybutene. Preferred are paraphenols with substituents of polypropylenes of $\overline{M}_n$ of about 170 to 800 or polybutenes of $\overline{M}_n$ of about 225 to 2100. These polymers are usually generated from refinery streams by polymerization in the presence of a suitable catalyst such as aluminum chloride. Processes for the alkylation of phenols to generate the desired reactants are widely known. See U.S. Pat. Nos. 2,398,253; 2,655,544; 2,671,117; and British Patent No. 1,159,368.

Because of their high viscosities of polymer substituted phenols are commonly diluted in an oil solvent to enable easy transport and handling. The amount of solvent varies widely. Commonly the diluent is used in such concentrations that achieve a suitable viscosity for the reaction mixture or product for ease of reaction and transfer while not unnecessarily diluting the final product. Suitable solvents include mineral lubricating oils of grades from light white oils to SAE-40. The diluent oils can be solvent extracted to avoid the presence of additives or impurities. SAE-5W is preferred as a diluent for the phenols used in the oxidation reaction.

Halogens appropriate to effect the oxidation include chlorine, bromine, and iodine. A molar amount of halogen that is equal to or exceeds the molar amount of phenol reactant is preferred. The halogen is added to the reaction mixture in elemental form as a gas at a rate of about 200-400 cc per minute (approximately 9-18 moles per minute) until no additional absorption occurs. Chlorine is preferred for the reaction because it is less expensive than the other halogens. In the manufacturing facility excess unreacted halogen could be recovered, separated from air, and recycled.

Suitable solvents for the reaction include inert hydrocarbons such as benzene, toluene, xylene or halogenated benzenes such as chlorobenzene, dichlorobenzene, and similar compounds. The particular solvent chosen is based on the temperature range desired for the reaction since the reaction is preferably carried out under refluxing conditions. As inert solvent such as benzene is preferred.

The halogen oxidation is base catalyzed reaction. Catalysts appropriate include metallic hydroxide compounds such as lithium hydroxide, sodium hydroxide, potassium hydroxide, magnesium hydroxide, and calcium hydroxide. Sodium hydroxide is preferred for economic reasons. The catalyst is usually added to the reaction mixture in solid form.

In somewhat greater detail the alkylated ortho-quinones are generated by oxidation of a monoalkylated phenol in a suitable solvent by the addition of a halogen compound as a gas in the presence of a base catalyst. The reaction can be carried out at atmospheric pressure at temperatures from 0° to 200° C., preferably at the refluxing temperature of the solvent. After completion of the reaction, the solvent can be separated by distillation of the reaction mixture and precipitated byproducts by filtration or other appropriate means of separating solids and liquids. The resulting quinone solution can then be concentrated by nitrogen sparging or equivalent means. The aliphatic substituent on the phenol reactant remains intact on the ortho-quinone generated.

To effect the oxidation reaction for generating ortho-quinones the alkylated phenol, an appropriate solvent such as benzene, and the base catalyst, preferably sodium hydroxide in solid form, are introduced into a conventional reaction vessel. The halogen gas, preferably chlorine, is introduced through a dispersion tube into the bottom of the reaction mixture at a rate of about 200 cc to 400 cc per minute (approximately 9-18 moles per minute). The amount of catalyst and halogen preferably each exceed the amount of phenol. Mole ratios of 1:1 to 6:1 catalyst to phenol and of 1:1 to 20:1 halogen to phenol can be used. Upon introduction of the halogen, heat is applied to the system with stirring to aid in generating contact and initiating the reaction.

The reaction can be carried out at temperatures of 0° C. to 200° C., preferably at the refluxing temperature of the solvent employed. The refluxing temperature is used as a means of controlling the reaction. Use of a lower temperature results in the disadvantage of a reduced reaction rate and longer reaction time while at higher temperatures the oxidation can be difficult to control. At the refluxing temperature the reaction can be conducted at atmospheric pressure.

The oxidation can be considered complete when the pH of the reaction mixture becomes acidic as demonstrated by a litmus test and free chlorine, no longer absorbed by the system, is emitted from the exhaust of the reactor. The reaction mixture is usually distilled to separate the solvent, yielding an azeotrope of solvent and water. Precipitated salt byproducts, such as metallic chlorides and bleach powder, can be removed by filtration or other equivalent means. The filtrate can then be concentrated by sparging with nitrogen or other inert gas up to 200° C. to yield the desired substituted ortho-quinone.

The halogenated ortho-quinone derivative can be generated either directly from the oxidation of the alkylated phenol or by halogenation of the alkylated ortho-quinone produced from the phenol oxidation. In the oxidation reaction a mole ratio of halogen to phenol of about 9 to 1 is normally used to produce ortho-quinone and of about 18 to 1 to produce halogenated ortho-quinone. All other reaction conditions and separation techniques required remain the same as previously described. To generate the halogenated ortho-quinone derivative from the corresponding alkylated ortho-quinone, standard methods of halogenation can be utilized or alternately the ortho-quinone can be treated in a manner analogous to the phenol in the oxidation reaction. This two step method permits use of a less expensive halogen to generate the quinone and substitution of a desired halogen in the latter halogenation reaction.

Yields of 50-95% quinone as measured by activities can be obtained using this process. The aliphatic substituent on the phenol reactant remains intact on the ortho-quinone generated. The phenol reactant therefore can be selected in accordance with the substituent desired on the ortho-quinone since no substantial change in the substituent occurs during the oxidation. Since ortho-quinones are used to intermediates to generate a wide variety of derivatives this attribute is an advantage in that it permits generation of the exact intermediate desired for a specific application.

One type of derivative which can be generated is dipolyolefin quinone compounds. This can be accomplished by adding polyalkylortho-quinone in acetic acid to a solution of potassium dichromate, manganese acetate, and water to effect an oxidative coupling reaction. The reaction can be used as a means of increasing the molecular weight of polymers containing an ortho-quinone. The dipolyalkylortho-quinones generated have the following structure:

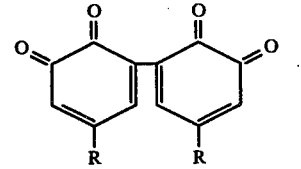

These compounds can be used as ultraviolet absorbers, insecticides, and intermediates for oxidation inhibitors.

A second type of derivative that can be generated from polyalkylortho-quinone is piperazine compounds useful as dispersants with special antioxidant properties. This can accomplished by adding bis-amino-propylpiperazine dropwise to a solution of monohalogenated polyalkylortho-quinone and then refluxing. Calcium hydroxide can be added to precipitate out chloride byproducts. Upon separation and concentration 1,4-bis, N,N'-dipolyalkylquinonyl aminoproply piperazine is obtained. This compound has the following structure:

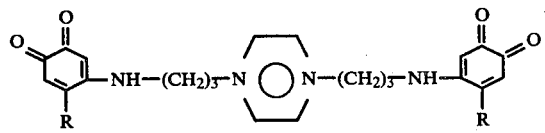

Spot dispersancy tests and varnish tests for oxidation have shown this compound to possess both dispersancy and antioxidant properties.

A class of antioxidants that can be produced from haloalkylortho-quinones is represented by the metallic dithiophosphonate derivative, such as zinc dithiophosphonate. This derivative can be made by first reacting haloalkylortho-quinone with phosphorus pentasulfide in an inert gas atmosphere and then after solvent removal adding a metallic nitrate slurry in oil to the reaction mixture. The resulting product is believed to be the following:

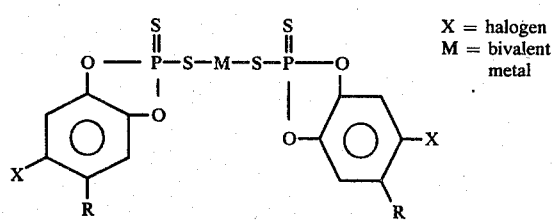

An oxidation inhibitor derivative can be generated by the reaction of haloalkylortho-quinone with sulfur monochloride. The product generated has the following structure:

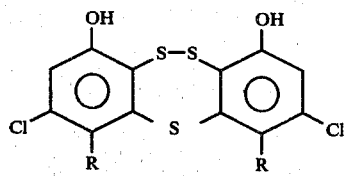

The condensation of alkylortho-quinones yields a compound which meets the structural demands of known compounds used as color preservatives in plastics. This product can be generated by reacting alkylortho-quinone with aluminum chloride in nitrobenzene. Upon chromatographic separation the condensation product obtained has the following structure:

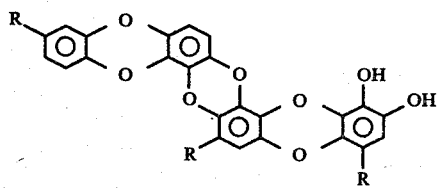

Another type of antioxidant can be generated by reacting alkylortho-quinone with ammonium acetate and paraformaldehyde under pressure. The product is an alkylated aza indene derivative with a molecular weight of about 570 with the following structure:

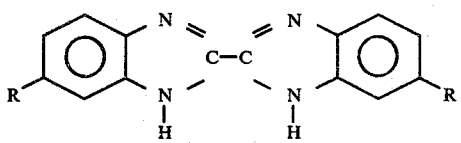

These are representative of the wide variety of derivatives that can be generated from the substituted quinone compounds of the present invention.

EXAMPLE 1

Approximately four moles of paradodecylphenol (1000 g) were dissolved in one liter of benzene in a reaction vessel equipped with a condensor and stirring device. Seven and one half moles (300 g) of solid sodium hydroxide are added. Chlorine gas with introduced at a rate of 200 cc per minute (approximately 9 moles per minute) throughout the reaction. Excess unreacted chlorine was not recovered for recycle. The reaction mixture was refluxed at approximately 80° C. for seven hours. Upon completion of the oxidation the reaction mixture was acidic as measured by a litmus test and free chlorine, no longer absorbed by the system, was emitted from the exhaust of the reactor. Distillation of the reaction solution gave an azeotrope of water and solvent. Sodium chloride and sodium hypochlorite precipitated and were removed by filtration. The quinone solution was concentrated by nitrogen sparging up to 150° C. yielding a dark red viscous liquid. Infrared analysis was performed upon a sample of the product and showed quinone and conjugated carboxyl absorption bands with no hydroxy absorptions and little or no aromatic substitution bands. The dodecylortho-quinone generated was dissolved in benzene, sodium hydroxide added, and the reaction mixture treated with chlorine gas at 400 cc per minute with refluxing as above. Separation and concentration of the reaction product as above yielded chlorododecylortho-quinone. Elemental analysis of the monochlorododecylortho-quinone for chlorine showed 11.5% present compared to a theoretical value of 11.3%. Chromatographic analysis gave 95% yield of quinone.

This example illustrates the production of dodecylortho-quinone and chlorododecylortho-quinone through chloro-oxidation of paradodecylphenol in the presence of a base catalyst. Dodecylortho-quinone and chlorododecylortho-quinone were also generated using a lower mole ratio of sodium hydroxide to dodecylphenol. Data is summarized in Table I.

Table I

| Example | 1a | 1b | 1c | 1d |
| --- | --- | --- | --- | --- |
| Moles Dodecylphenol | 4 | 4 | 4 | 4 |
| Moles NaOH | 7.5 | 7.5 | 7.5 | 5 |
| Solvent | Benzene | Benzene | Benzene | Benzene |
| Temp. °C. | 80 | 80 | 80 | 80 |
| Yield of Quinone | 95% | 71% | 65% | 66% |

EXAMPLE 2

This example illustrates the production of polybutylortho-quinone and chloropolybutylortho-quinone using the method of Example 1. One half mole of parapolybutylphenol ($\overline{M}_n$ 1600) in 50% 5W oil was dissolved in one liter of toluene in a conventional glass reactor equipped as in Example 1. Three moles (120 g) of solid sodium hydroxide were added to the solution and chlorine gas introduced at a rate of 200 cc per minute (approximately 9 moles per minute). The reaction mixture was refluxed at temperatures of 95°–125° C. for five to seven hours. At the completion of the oxidation the reaction mixture was acidic as measured by a litmus test and free chlorine, no longer absorbed by the system, was emitted from the exhaust of the reactor. The desired polybutylortho-quinone was separated as in Example 1 and identified by infrared spectroscopy. Chloropolybutylortho-quinone was then generated as in Example 1. Elemental analysis for chlorine was performed to verify product identification. Polybutylortho-quinone and chloropolybutylortho-quinone were also generated using lower mole ratios of sodium hydroxide to polybutylphenol. Data is summarized in Table II.

Table II

| Example | 2a | 2b | 2c |
|---|---|---|---|
| Moles Polybutylphenol | 0.5 | 0.5 | 0.5 |
| Moles NaOH | 3.0 | 2.0 | 1.0 |
| Solvent | Toluene | Benzene | Benzene |
| Temp. °C. | 115 | 80 | 80 |
| Yield of Quinone | 90% | 60% | 53% |

EXAMPLE 3

This example illustrates the production of di-polybutyl quinones by an oxidative coupling reaction. Polybutylortho-quinone was made according to the procedure of Example 2. One half mole (1385 g) of polybutylquinone in 5W oil was dissolved in acetic acid. This was added slowly to a stirrred solution of 88 g (0.3 mole) of potassium dichromate, 30 g of manganese acetate, and 40 cc of water in a conventional glass reactor. The reaction mixture was heated and refluxed at approximately 120° C. until the color turned green indicating oxidation had occurred. The product was washed to remove acid and salts. The average molecular weight of the product recovered was 3085 and its activity was 55%. The product was identified by infrared spectroscopy. The dipolybutyl quinones are useful as ultraviolet absorbers, insecticides, and as intermediates to generate oxidation inhibitors. In addition this reaction process can be used to increase the molecular weight of polymers containing ortho-quinones.

EXAMPLE 4

This example illustrates the production of the derivative 1,4 bis-N,N'-dipolybutylquinoyl aminopropylpiperazine. To the reaction mixture of Example 2 containing chloropolybutylortho-quinone after removal of water by azeotropic distillation 50 g (¼ mole) of bis-aminopropylpiperazine were added dropwise. The reaction mixture was then heated under reflux conditions at about 115° C. for one hour. To remove chloride by-products 37 g of calcium hydroxide in 600 cc of 5W oil were added to the reaction mixture and the reaction was continued for an additional two hours. The mixture was filtered hot over celite to separate the chlorides and concentrated by stripping with nitrogen. Elemental test for nitrogen showed 1.33% present compared to a theoretical amount of 1.63%. The compound had an activity of 45%. The dispersancy and antioxidant properties of the compound were confirmed by analytical testing. A spot dispersancy test result of 92 compared to a standard of 85 was obtained. In a hot tube varnish test for oxidation a score of 8.5A on a scale where 10A is perfect was obtained.

EXAMPLE 5

This example illustrates production of the zinc dithiophosphonate derivative of chlorododecylorthoquinone. One and one half moles (490 g) of monochlorododecyl ortho-quinone from Example 1 were dissolved in 500 ml of benzene and 300 g of phosphorus pentasulfide were added slowly under an atmosphere of nitrogen. The reaction mixture was refluxed at about 80° C. and solvent then removed by distillation up to 120° C. and nitrogen purging. A slurry of 149 g of zinc nitrate of 250 ml of 5W oil was added to the reaction mixture. The reaction was continued at 150° C. and again purged with nitrogen for one hour to remove nitrous fumes. The product was separated by filtration over celite. A 60% conversion was obtained. Elemental analysis showed the presence of 14.5% sulfur, 7.2% zinc, and 6.8% phosphorus. The corresponding theoretical values are 14.6% sulfur, 7.4% zinc, and 7.1% phosphorus. This derivative is useful as an antioxidant.

EXAMPLE 6

This example illustrates the reaction of substituted ortho-quinones with sulfur monochloride to generate dibenzo [c,f][1,2,5] trithiepin (1,10-dialkyl-2,9-dichloro-4,7 dihydroxy). Approximately one half mole (160 g) of chlorododecylortho-quinone from Example 1 was dissolved in 300 ml of benzene and one mole (135 g) of sulfur monochloride was added. The reaction mixture was refluxed for four hours at about 80° C. and product was recovered by stripping the solvent with nitrogen and filtering over celite. Elemental analysis of the product showed the presence of 12.4% sulfur and 11.9% chlorine compared to theoretical values of 14.0% for sulfur and 11.9% for chlorine. The product is useful as an oxidation inhibitor.

EXAMPLE 7

This example illustrates the condensation of alkylated ortho-quinones. To 366 gm of dodecylortho-quinone prepared as in Example 1 in 100 ml of nitrobenzene 66.5 g of anhydrous aluminum chloride were added. The reaction was stirred for six hours at 65° C. A slow evolution of hydrochloride gas occurred. After chromatographic separation a 10% product yield was obtained. The product was identified by infrared spectroscopy and was found to meet the structural demands of known compounds used as color preservatives in plastics.

EXAMPLE 8

This example illustrates the production of an alkylated aza indene derivative useful as an antioxidant. Forty grams of dodecylortho-quinone prepared as in Example 1 was reacted with thirty grams of ammonium acetate and ten grams of paraformaldehyde under 5 pounds of pressure at 150° C. for 2 hours. The alkylated aza indene product was 99% active and had a molecular weight of 568. The product was identified by infrared spectroscopy.

I claim:

1. An ortho-quinone having the structure:

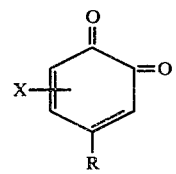

wherein R is an alkyl chain of at least 12 carbon atoms or a polymer of an olefin of at least three carbon atoms; and X is selected from the group consisting of hydrogen, chlorine, bromine, and iodine.

2. The composition of claim 1 wherein R is polybutene of $\overline{M}_n$ of about 225 to 2100.

3. The composition of claim 1 wherein R is polypropylene of $\overline{M}_n$ of about 170 to 800.

4. The composition of claim 1 wherein R is dodecyl.

5. The composition of claim 1 wherein X is chlorine.

* * * * *